United States Patent
Iitsuka et al.

(10) Patent No.: US 9,573,862 B2
(45) Date of Patent: Feb. 21, 2017

(54) METHOD FOR CONVERTING OLEFIN OR ALCOHOL AND METHOD FOR PRODUCING PROPYLENE OR AROMATIC COMPOUND

(71) Applicant: ASAHI KASEI CHEMICALS CORPORATION, Tokyo (JP)

(72) Inventors: Takehiro Iitsuka, Tokyo (JP); Yoshikazu Takamatsu, Tokyo (JP)

(73) Assignee: ASAHI KASEI CHEMICALS CORPORATION, Tokyo (JP)

(*) Notice: Subject to any disclaimer, the term of this patent is extended or adjusted under 35 U.S.C. 154(b) by 68 days.

(21) Appl. No.: 14/419,135

(22) PCT Filed: Aug. 9, 2013

(86) PCT No.: PCT/JP2013/071684
§ 371 (c)(1),
(2) Date: Feb. 2, 2015

(87) PCT Pub. No.: WO2014/025021
PCT Pub. Date: Feb. 13, 2014

(65) Prior Publication Data
US 2015/0152024 A1     Jun. 4, 2015

(30) Foreign Application Priority Data
Aug. 10, 2012 (JP) ................... 2012-178398

(51) Int. Cl.
*C07C 2/42* (2006.01)
*B01J 21/08* (2006.01)
(Continued)

(52) U.S. Cl.
CPC ............... *C07C 2/42* (2013.01); *B01J 8/0055* (2013.01); *B01J 8/1809* (2013.01); *B01J 21/08* (2013.01);
(Continued)

(58) Field of Classification Search
None
See application file for complete search history.

(56) References Cited

U.S. PATENT DOCUMENTS

| 4,567,310 A | 1/1986 | Rodewald |
| 5,106,486 A | 4/1992 | Hettinger |

(Continued)

FOREIGN PATENT DOCUMENTS

| CN | 101695674 A | 4/2010 |
| JP | 61-187935 A | 8/1986 |

(Continued)

OTHER PUBLICATIONS

The International Preliminary Report on Patentability and an English translation of the Written Opinion of the International Searching Authority, dated Feb. 19, 2015, issued in the corresponding International Application No. PCT/JP2013/071684.
(Continued)

*Primary Examiner* — Tam M Nguyen
(74) *Attorney, Agent, or Firm* — Birch, Stewart, Kolasch & Birch, LLP

(57) ABSTRACT

A method for converting an olefin or an alcohol has a pretreatment step of obtaining a conductive catalyst by a pretreatment for suppressing electrostatic charging of a non-conductive catalyst and a step of converting an olefin or an alcohol by a fluidized bed reaction using the conductive catalyst.

7 Claims, 9 Drawing Sheets

(51) Int. Cl.
| | |
|---|---|
| B01J 29/40 | (2006.01) |
| B01J 8/18 | (2006.01) |
| B01J 8/00 | (2006.01) |
| C07C 1/20 | (2006.01) |
| B01J 37/10 | (2006.01) |
| B01J 37/28 | (2006.01) |
| B01J 29/06 | (2006.01) |
| B01J 29/064 | (2006.01) |
| B01J 35/00 | (2006.01) |
| B01J 37/00 | (2006.01) |
| B01J 37/08 | (2006.01) |
| B01J 29/068 | (2006.01) |
| C07C 6/04 | (2006.01) |
| C07C 2/76 | (2006.01) |
| C10G 3/00 | (2006.01) |
| B01J 38/00 | (2006.01) |
| B01J 38/14 | (2006.01) |
| B01J 38/30 | (2006.01) |

(52) U.S. Cl.
CPC ............ *B01J 29/061* (2013.01); *B01J 29/064* (2013.01); *B01J 29/068* (2013.01); *B01J 29/40* (2013.01); *B01J 35/0026* (2013.01); *B01J 35/0033* (2013.01); *B01J 37/0045* (2013.01); *B01J 37/084* (2013.01); *B01J 37/105* (2013.01); *B01J 37/28* (2013.01); *C07C 1/20* (2013.01); *C07C 2/76* (2013.01); *C07C 6/04* (2013.01); *C10G 3/44* (2013.01); *C10G 3/49* (2013.01); *C10G 3/57* (2013.01); *C10G 3/60* (2013.01); *B01J 38/00* (2013.01); *B01J 38/14* (2013.01); *B01J 38/30* (2013.01); *B01J 2208/0007* (2013.01); *B01J 2208/00584* (2013.01); *B01J 2208/00681* (2013.01); *B01J 2208/00734* (2013.01); *B01J 2229/12* (2013.01); *B01J 2229/186* (2013.01); *B01J 2229/34* (2013.01); *B01J 2229/36* (2013.01); *B01J 2229/40* (2013.01); *B01J 2229/42* (2013.01); *C07C 2529/40* (2013.01); *C10G 2300/703* (2013.01); *C10G 2400/20* (2013.01); *C10G 2400/30* (2013.01); *Y02P 20/52* (2015.11); *Y02P 20/582* (2015.11); *Y02P 20/584* (2015.11)

(56) References Cited

U.S. PATENT DOCUMENTS

| | | |
|---|---|---|
| 2012/0203048 A1 | 8/2012 | Hayashi et al. |
| 2013/0231515 A1 | 9/2013 | Akagishi et al. |
| 2013/0292695 A1 | 11/2013 | Horii et al. |

FOREIGN PATENT DOCUMENTS

| | | |
|---|---|---|
| JP | 2-91030 A | 3/1990 |
| JP | 7-84598 B2 | 9/1995 |
| JP | 9-94460 A | 4/1997 |
| JP | 2004-345972 A | 12/2004 |
| JP | 2005-232123 A | 9/2005 |
| JP | 2011-011207 A | 1/2011 |
| JP | 2011-78962 A | 4/2011 |
| JP | 2012-120978 A | 6/2012 |
| JP | 2012-166157 A | 9/2012 |
| WO | WO 2010/016388 A1 | 2/2010 |
| WO | WO 2011/054203 A1 | 5/2011 |
| WO | WO 2012/070605 A1 | 5/2012 |

OTHER PUBLICATIONS

The International Search Report, dated Nov. 12, 2013, issued in the corresponding International Application No. PCT/JP2013/071684.
European Search Report, issued Oct. 6, 2015, for European Application No. 13827983.1.

US 9,573,862 B2

METHOD FOR CONVERTING OLEFIN OR ALCOHOL AND METHOD FOR PRODUCING PROPYLENE OR AROMATIC COMPOUND

TECHNICAL FIELD

The present invention relates to a method for converting an olefin or an alcohol and a method for producing propylene or an aromatic compound.

BACKGROUND ART

Many methods are known for producing propylene and an aromatic hydrocarbon from a hydrocarbon as a starting material by a fluidized bed reaction. For example, Patent Literature 1 discloses a method for producing propylene using a zeolite-containing catalyst containing a zeolite and silica.

CITATION LIST

Patent Literature

Patent Literature 1: International Publication No. WO 2010/016388

SUMMARY OF INVENTION

Technical Problem

According to the technique described in Patent Literature 1, it is found that even if a fluidized bed reaction using a catalyst containing a zeolite and silica is experimentally carried out in a small scale equipment, substantial troubles would not occur. However, the present inventors found that if such a fluidized bed reaction is carried out in a scale-up reactor, a phenomenon where catalyst particles deposit on the inner wall of the reactor occurs. The present inventors studied on the cause of this phenomenon. As a result, they found that when a catalyst containing a component having high electric resistivity, such as a zeolite and silica, as a main component is used in the fluidized bed reaction, static electrical charge occurs due to friction among catalyst particles, the reactor and a reaction gas, and the catalyst is charged. The charged catalyst tends to deposit on the inner wall of a reactor. If the charged catalyst deposits on the reactor, flowability of the catalyst significantly reduces and the reaction results become poor. Furthermore, the catalyst deposited near the outlet of the reactor easily flows out together with a produced gas (adjoint outflow) toward an outlet pipe of the reactor. As a result, catalyst loss increases.

The present invention was made in consideration of the aforementioned problems. To be more specific, an object of the present invention is to provide a method for converting an olefin or an alcohol and a method for producing propylene or an aromatic compound, which can suppress electrostatic charging of a catalyst or deposition of a catalyst to a reactor and can successfully realize an excellent reaction efficiency.

Solution to Problem

The present inventors conducted intensive studies with a view to solving the aforementioned problems. As a result, they found that the problems can be overcome by applying a pretreatment for suppressing electrostatic charging of a non-conductive catalyst, and arrived at accomplishment of the present invention.

More specifically, the present invention is as follows:

[1] A method for converting an olefin or an alcohol, comprising:
a pretreatment step of obtaining a conductive catalyst by a pretreatment for suppressing electrostatic charging of a non-conductive catalyst; and
a step of converting the olefin or the alcohol by a fluidized bed reaction using the conductive catalyst.

[2] The method for converting the olefin or the alcohol according to [1], wherein the pretreatment step comprises depositing a conductive substance to the non-conductive catalyst.

[3] The method for converting the olefin or the alcohol according to [1] or [2], wherein, in the pretreatment step, the non-conductive catalyst having an electrostatic deposition rate of 15 mass % or more is used.

[4] The method for converting the olefin or the alcohol according to any one of [1] to [3], wherein the non-conductive catalyst comprises a zeolite and/or silica.

[5] The method for converting the olefin or the alcohol according to any one of [2] to [4], wherein the conductive substance comprises carbon.

[6] The method for converting the olefin or the alcohol according to any one of [1] to [4], wherein the olefin comprises ethylene.

[7] A method for producing propylene or an aromatic compound, comprising a step of obtaining propylene or the aromatic compound by the method according to any one of [1] to [6].

Advantageous Effects of Invention

According to the present invention, electrostatic charging of a catalyst or deposition of a catalyst to a reactor can be suppressed in converting an olefin or an alcohol and producing propylene or an aromatic compound, and excellent reaction efficiency can be realized.

DESCRIPTION OF EMBODIMENTS

Figure 1:
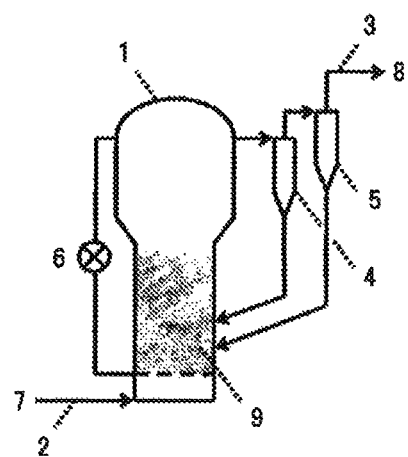
FIG. 1 shows a schematic view of a pilot-scale fluidized bed reactor for carrying out a fluidized bed reaction.

Now, an embodiment for carrying out the invention (hereinafter referred to as "the present embodiment") will be more specifically described below. The present invention is not limited to the following descriptions and can be modified in various ways within the scope of the invention. Note that in the specification, "silica" refers to silica to be used as a carrier for a non-conductive catalyst containing a zeolite and does not refer to silica constituting a zeolite and a clay mineral, unless otherwise specified. Similarly "alumina" refers to alumina to be used as a carrier for a non-conductive catalyst containing a zeolite and does not refer to alumina constituting a zeolite and a clay mineral, unless otherwise specified.

The method for converting an olefin and an alcohol according to the present embodiment has a pretreatment step of obtaining a conductive catalyst by a pretreatment for suppressing electrostatic charging of a non-conductive catalyst, and a step of converting an olefin or an alcohol by a fluidized bed reaction using the conductive catalyst. Owing to the constitution, the method for converting an olefin or an alcohol according to the present embodiment can suppress electrostatic charging of a catalyst or deposition of a catalyst to a reactor, and thus excellent reaction efficiency can be realized.

[Fluidized Bed Reaction]

In the present embodiment, "fluidized bed reaction" refers to a reaction performed using a fluidized bed reactor in a layer containing a catalyst filled in the reactor and floated (fluidized) with a gas supplied from a lower part of the reactor. Examples of the fluidized bed reactor may include, but not particularly limited to, a vertical cylindrical container which has at least one gas distributor for feeding out a process feed gas, provided at a predetermined position in a reactor bed, an interior coil for removing or adding heat as necessary, and an exterior or interior cyclone for limiting adjoint outflow of a catalyst to a minimum, as necessary. Examples of the gas distributor may include a gas diffusion board having many micro pores. In order to reduce a gas velocity for limiting adjoint outflow of catalyst particles to a minimum, a fluidized bed reactor having an expanded portion on the top can be used. The catalyst particles are fluidized by the gas supplied from the gas distributor. Furthermore, if the gas and catalyst particles are in close contact with each other, satisfactory heat transfer/substance migration between a gas phase and a solid phase is ensured. As a result, the temperature in the fluidized bed reactor is kept homogenously. The reaction heat may be controlled by the coil and water jacket provided in the reactor and fluidizing gas itself or other heat transfer mediums.

In the present embodiment, in order to maintain a satisfactory mixing state of the gas and catalyst particles to ensure sufficiently satisfactory reaction results, it is preferable that the gas is supplied at an appropriate rate. If the gas supply rate is controlled within an appropriate range, sufficient fluidization of catalyst particles can be ensured and thus the gas and the catalyst tend to be sufficiently mixed. If the gas supply rate is gradually increased, the gas, which previously just passes through the spaces between catalyst particles, changes into bubbles, which move upward in the reactor. As a result, the behaviors of the catalyst particles tend to be pushed up, pushed away and/or pulled up by the bubbles moving upward. In short, if the gas supply rate is controlled to fall within an appropriate range, a satisfactory mixing state is obtained and reaction results tend to improve. Note that, generally, if a gas supply rate increases, the catalyst particles fall in the state called slugging and finally flow out together with the gas, thereby catalyst loss tends to increase. The "slugging" herein refers to the state where a whole catalytic bed repeatedly moves up and down while keeping a clump and causes pressure fluctuation. For example, in "Fluidized Bed Handbook" (edited by the Powder Process Industry & Engineering, Japan, BAIFU-KAN CO., LTD., 1999), p. 17, the gas flow rate in operating a fluid catalyst reaction process is described as follows: "Operation should be made at a gas flow rate of 0.2 to 98 m·s$^{-1}$ so as to obtain a turbulence state in the layer". In view of this, it is preferable that the gas supply rate in terms of the gas flow rate in the reactor is 0.5 m/sec or more and 2.0 m/sec or less, for the purpose of performing conversion of an olefin or an alcohol by a fluidized bed reaction in the present embodiment.

FIG. 1 schematically shows one example of a pilot-scale fluidized bed reactor for carrying out a fluidized bed reaction. In the pilot-scale fluidized bed reactor, a feed gas 7 is supplied by a gas supply pipe 2 from the lower portion of a fluidized bed reactor 1. A catalytic bed 9, which is fluidized by the feed gas 7, is allowed to be in contact with the feed gas 7 to react with the gas. The fluidized catalyst is separated from the gas by #1 cyclone 4 and #2 cyclone 5 provided in the upper portion of the reactor. The separated gas is discharged as a product gas 8 through a pipe 3 provided downstream of the reactor. The fluidized bed reactor 1 has a differential pressure gage 6, which is provided in order to check the mass of the catalyst stored in the fluidized bed reactor and monitor stability of the catalyst fluidization state.

[Electrostatic Charging/Triboelectric Charging]

In the present embodiment, "electrostatic charging" refers to triboelectric charging generated between two different substances when they are in close contact with each other. Hereinafter, the electrostatic charging is also referred to simply as "charging". The two different substances are, for example, two different metals (conducting bodies), two different insulating bodies (for example, wool versus amber rod) or a conducting body and an insulating body. In the case of a fluidized bed reaction using a non-conductive catalyst as in the present embodiment, examples of an evaluation target for electrostatic charging may include triboelectric charging generated by friction contact of non-conductive catalyst particles (insulating body) with carbon steel (conducting body) forming a reactor wall. The strong or weak driving power basically generated by triboelectric charging is derived from difference in affinity for electrons between two substances. The substance having a larger affinity receives electrons and is negatively charged. In contrast, the other substance loses electrons and is positively charged. The amount of charges moving by bombardment between metallic portions, such as the wall, pipes or other members of a fluidized bed reactor, and solid particles varies depending upon e.g., electric properties, the degree of contact and surface roughness of the metallic portions and the particles.

Troubles of the catalyst in connection with electrostatic charging in the reactor are particularly likely to come up in a fluidized bed reactor of an industrial scale. In the case of the industrial-scale fluidized bed reactor, a gas flow rate in the reactor for operation generally falls within the range of about 0.2 m/sec or more and 98 m/sec or less. However, if the gas flow rate in the reactor is 0.40 m/sec or more, the catalytic bed falls in a turbulence state and electrostatic charging comes to easily occur. Accordingly, the method for converting an olefin or an alcohol of the present embodiment is particularly preferably used in the case of a reaction performed using an industrial scale fluidized bed reactor at a gas flow rate of 0.40 m/sec or more.

Note that a trouble with electrostatic charging does not become apparent in a small equipment in most cases in experiments. For example, in experimental conditions as disclosed in Patent Literature 1 (Example 27), more specifically, at a gas flow rate (in the reactor) of 0.02 m/sec, electrostatic charging is low. Thus, the trouble due to catalyst deposition to the reactor rarely becomes apparent.

[Non-Conductive Catalyst]

In the present embodiment, the "non-conductive catalyst" refers to a catalyst having an electrostatic deposition rate of 15 mass % or more which is obtained by an electrostatic deposition rate measuring method (described later). Examples of the catalyst having a large electrostatic deposition rate may include a catalyst containing e.g., a zeolite and/or silica as components. A zeolite, since it has a satisfactory catalyst activity in producing an olefin, is preferably used. Silica is also preferably used as a component (also referred to as a carrier or a binder) for providing strength as a fluidized-bed catalyst. In the present embodiment, the non-conductive catalyst may contain, other than a zeolite and silica, another component such as a transition metal and a phosphorus compound, in order to improve e.g., reactivity, hydrothermal stability and strength.

The non-conductive catalyst is not particularly limited; however, it is preferable that the particles of the catalyst have suitable properties in order to attain a satisfactory fluidization state in a fluidized bed reaction process. For example, in "Fluidized Bed Handbook (edited by the Powder Process Industry & Engineering, Japan, BAIFUKAN CO., LTD., 1999)", p. 16, there is a description reading "moving substances at a sufficiently high speed to an emulsion phase containing bubbles and a catalyst is desirable to improve a reaction rate and selectivity. For achieving this, bubbles are preferably small and particles are preferably small and smooth in surface". Generally, in accordance with fluidization of a catalyst, abrasion and breakup of catalyst particles may sometimes occur by bombardment and contact between catalyst particles, between catalyst particles and a reactor, between catalyst particles and reaction gas, etc. To effectively prevent flowability reduction of catalyst particles and scattering of broken particles due to abrasion and breakup of the catalyst particles, it is preferable that the fluidized-bed reaction catalyst has sufficient mechanical strength enough to resist abrasion and breakup.

The content of a zeolite in a non-conductive catalyst, in view of reactivity and strength, preferably falls within the range of 10 mass % or more and 90 mass % or less based on the total mass of the catalyst, and more preferably 20 mass % or more and 80 mass % or less. If the content of a zeolite is 10 mass % or more, sufficient reactivity of a catalyst tends to be ensured. In contrast, if the content is 90 mass % or less, sufficient strength of a catalyst tends to be ensured.

[Conductive Catalyst/Conductive Substance]

In the present embodiment, the "conductive catalyst" refers to a catalyst obtained by reducing the electrostatic deposition rate of a non-conductive catalyst, and more specifically, a catalyst having an electrostatic deposition rate of less than 15 mass %, which is obtained by an electrostatic deposition rate measuring method (described later).

In the present embodiment, the conductive catalyst to be used in a fluidized bed reaction may contain a non-conductive catalyst as a part. Alternatively, after a non-conductive catalyst is subjected to a pretreatment step and changed into a conductive catalyst, the resultant catalyst may be mixed with a non-conductive catalyst. However, the mixing ratio is appropriately controlled such that an electrostatic deposition rate of the entire catalyst after the non-conductive catalyst is added becomes less than 15%.

The "conductive substance" refers to a substance containing a component having a low electrical resistivity as a main component. Examples of the conductive substance may include a carbon-based conductive substance, a metal-based conductive substance, an inorganic-based conductive substance, water and an antistatic agent (surfactant, etc.). Examples of the carbon-based conductive substance may include, but not particularly limited to, precipitated coke, carbon black, carbon fibers and graphite. Examples of the metal-based conductive substance may include, but not particularly limited to, metal fine powders, metal oxides and metal fibers. Examples of the inorganic-based conductive substance may include, but not particularly limited to, glass beads and synthetic fibers.

[Pretreatment Step of Obtaining a Conductive Catalyst by a Pretreatment for Suppressing Electrostatic Charging of a Non-Conductive Catalyst]

In the present embodiment, the "pretreatment step of obtaining a conductive catalyst by a pretreatment for suppressing electrostatic charging of a non-conductive catalyst" is not particularly limited, as long as the step includes suppressing electrostatic charging of a non-conductive catalyst. The pretreatment step is preferably a step of suppressing electrostatic charging by physically and chemically providing conductivity to a catalyst before subjected to a reaction, and more preferably, a step of obtaining a conductive catalyst by depositing a conductive substance to a non-conductive catalyst. In a case that a conductive substance is deposited to a non-conductive catalyst, the electrostatic deposition rate of the non-conductive catalyst can be controlled by controlling the deposition amount of conductive substance. Hereinafter, "the pretreatment step of obtaining a conductive catalyst by a pretreatment for suppressing electrostatic charging of a non-conductive catalyst" is also referred to simply as the "pretreatment step".

In the pretreatment step, a conductive substance is deposited to a molded non-conductive catalyst by a method such as simple mixing, surface coating or kneading. Examples of the surface coating may include deposition by precipitation, plating, spray coating and coating. After a large amount of a conductive substance is deposited, excessive conductive substances may be appropriately removed. This is, for example, the case where only an excessive carbonaceous compound (coke) is removed by incineration in a step of regenerating a catalyst (described later). The non-conductive catalyst is evaluated as a conductive catalyst, if the non-conductive catalyst is treated in the pretreatment step to reduce the electrostatic deposition rate of the non-conductive catalyst up to less than 15 mass %, which is measured by the electrostatic deposition rate measuring method (described later) of a catalyst.

The pretreatment step can be performed, for example, by use of a muffle furnace, a rotary oven, a tunnel furnace, a tubular furnace, a fluidized bed furnace, a kiln furnace and a fluidized bed reactor. The pretreatment step is performed before a fluidized bed reaction; however, in order to effectively moving into the fluidized bed reaction from the pretreatment step, the pretreatment step is preferably performed in the same fluidized bed reactor as used for a fluidized bed reaction.

Now, one example of the pretreatment step, in which a non-conductive catalyst is used as a catalyst for a fluidized-bed reaction for producing propylene or an aromatic compound by bringing the catalyst in contact with a hydrocarbon starting material containing ethylene, will be described below.

The fluidized bed reactor 1 shown in FIG. 1 for carrying out a fluidized bed reaction is charged with a non-conductive catalyst. A heated hydrocarbon gas is supplied to the fluidized bed reactor 1 and brought into contact with the non-conductive catalyst in the fluidized bed reactor 1 at a temperature of 300 to 650° C. under a pressure of 0.01 to 3.0 MPa·G to precipitate carbonaceous coke and deposit on the non-conductive catalyst. The precipitation deposition amount of the carbonaceous coke can be controlled by monitoring a change of catalyst mass based on the indication by the differential pressure gage 6 provided to the fluidized bed reactor 1. The gas supply rate at this time is preferably 0.40 m/sec or less in terms of gas flow rate in the reactor. Electrostatic charging occur due to friction between the non-conductive catalyst, a reactor and a feed gas; however, electrostatic charging of the non-conductive catalyst tends to be effectively suppressed in the pretreatment step by performing the pretreatment step at a gas flow rate purposely lower than that in the fluidized bed reaction. Note that gas flow rate in the reactor can be obtained in accordance with the following formula.

Gas flow rate [m/sec]=feed-gas flow volume [m$^3$/sec]/cross-sectional area of reactor [m$^2$]

[Step of Regenerating Catalyst in Fluidized Bed Reaction]

If a catalyst is used in a reaction for a long time, the activity of the catalyst can be reduced by excessive production of a carbonaceous compound (coke) on the catalyst. In order to regenerate (reactivate) the catalyst to regain the reduced activity, a whole or part of the catalyst is removed from the reactor and a treatment of removing coke deposited on the catalyst by burning it may be appropriately performed.

When the coke deposited on the catalyst is removed by burning, the electrostatic deposition rate increases and the regenerated catalyst tends to become a non-conductive catalyst. For the reason, it is preferable that excessive coke alone is removed by incineration while appropriately controlling calcination conditions such as temperature and time to maintain an electrostatic deposition rate of less than 15%. When the catalyst is regenerated into a non-conductive catalyst, it is preferable that the regenerated catalyst is subjected to the pretreatment step before the catalyst is returned to the reactor to convert into a conductive catalyst, which is then returned to the reactor. Alternatively, a method of mixing a conductive catalyst and a non-conductive catalyst may be employed. In this case, care must be taken for a regeneration amount of the catalyst, in other words, control should be made so as to obtain an electrostatic deposition rate of less than 15% even if the regenerated catalyst is returned.

[Method for Converting Olefin or Alcohol]

In the present embodiment, the method for converting an olefin or an alcohol includes a step of bringing the conductive catalyst obtained through the pretreatment step into contact with an olefin or an alcohol in a fluidized bed reactor. In order to produce propylene and an aromatic compound in high yield, the number of carbon atoms of an olefin or an alcohol serving as a starting material preferably falls within the range of 2 or more and 12 or less. An olefin may be used in combination with an alcohol. Furthermore, from the same point of view, ethylene is more preferably included as an olefin.

In the present embodiment, an olefin or an alcohol serving as a starting material for a reaction is not necessary to have a high purity and is satisfactory if it is an industrial glade. In the present embodiment, the starting material for a reaction to be used in the method for converting an olefin or an alcohol contains ethylene in an amount of preferably 20 mass % or more and more preferably 25 mass % or more, in view of reaction efficiency. Furthermore, the case where an olefin or an alcohol is supplied together with water vapor to a reactor is preferable since a step of separating and recovering water contained in the starting material can be omitted. In this case, the supply rate of water vapor is preferably 1 mass % or more, more preferably 5 mass % or more and 60 mass % or less and further preferably 10 mass % or more and 50 mass % or less, since a product obtained by e.g., steam cracking and a dewatering reaction of an alcohol is used as the starting material of a reaction. Note that in the method for converting an olefin or an alcohol in the present embodiment, a desired product (for example, propylene and an aromatic compound) is separated from reaction products, at least a part of the remaining low boiling-point components containing ethylene and/or high boiling-point components containing butene is supplied to a fluidized bed reactor as a starting material for recycle use. This is one of preferable embodiments.

In the present embodiment, the starting material for an olefin is not particularly limited, for example, olefins obtained by thermolysis, steam cracking and an oxidative dehydrogenation reaction of ethane, and a dehydration reaction of an alcohol can be used. The starting material for a reaction may contain an olefin and a paraffin. Examples of the paraffin may include, but not particularly limited to, methane, ethane, propane, butane, pentane, hexane, heptane, octane and nonane. Examples of the olefin may include, but not particularly limited to, ethylene, propylene, butene, pentene, hexene, heptene, octene and nonene. The starting material for an olefin, in addition to the aforementioned compounds, may contain a cycloparaffin such as cyclopentane, methyl cyclopentane and cyclohexane; a cycloolefin such as cyclopentene, methylcyclopentene and cyclohexene; a diene such as cyclohexadiene, butadiene, pentadiene and cyclopentadiene; and/or an acetylene such as acetylene and methylacetylene. The starting material for an alcohol may contain an oxygen-containing compound such as t-butyl alcohol, methyl-t-butyl ether, diethyl ether, methyl ethyl ether, dimethyl ether, ethanol and methanol. Furthermore, an olefin or an alcohol may further contain water, hydrogen, nitrogen, carbon dioxide and carbon monoxide.

In the case where a starting material for a reaction contains ethanol, ethanol obtained from plant resources (biomass ethanol) can be used as the starting material. Examples of the biomass ethanol may include ethanol obtained by fermentation of sugar cane and corn; and ethanol obtained from ligneous resources such as scrap wood, thinning materials, rice straw and farm products.

The reaction temperature of the fluidized bed reaction is preferably 300° C. or more and 650° C. or less, and more preferably 400° C. or more and 600° C. or less, in order to produce propylene and an aromatic compound in high yield. Furthermore, from the same point of view, the reaction pressure is preferably 0.01 MPa·G or more and 3.0 MPa·G or less and more preferably 0.05 MPa·G or more and 1.0 MPa·G or less.

The supply rate of a starting material for a reaction, is preferably 0.1 hr$^{-1}$ or more and 20 hr$^{-1}$ or less, and more preferably 0.5 hr$^{-1}$ or more and 10 hr$^{-1}$ or less, in terms of Weight Hourly Space Velocity (WHSV) based on the catalyst, in order to produce propylene and an aromatic compound in high yield.

In the method for converting an olefin or an alcohol by the fluidized bed reaction according to the present embodiment, the conversion rate of ethylene can be controlled when an ethylene-containing starting material is used by controlling the above reaction conditions. For example, the ethylene conversion rate can be preferably controlled to fall within the range of 45 to 85 mass % and preferably 50 to 80 mass %.

[Zeolite]

In the present embodiment, "zeolite" refers to a crystalline porous aluminosilicate or a metallosilicate and also includes a phosphate-based porous crystal having the same or analogous structure to them. Note that the metallosilicate refers to a zeolite obtained by replacing a whole or part of aluminum atoms constituting the skeleton of a crystalline porous aluminosilicate with replaceable elements such as Ga, Fe, B, Cr and Ti. More specifically, examples of the zeolite having a small pore diameter (structure of oxygen 8-membered ring or less) may include chavazite ("CHA", notation of a zeolite according to a classification code depending upon the structure defined by the international zeolite academy. Hereinafter the same notation is employed), erionite (ERI) and Linde type A (LTA). Examples of the zeolite having a medium pore diameter (structure of oxygen 10-membered ring) may include ferrierite (FER), MCM-22 (MWW), ZSM-11 (MEL), ZSM-5 (MFI) and AlPO$_4$-11 (AEL). Examples of the zeolite having a large pore diameter (structure of oxygen 12-membered ring) may include type L (LTL), type X (FAU), type Y (FAU), faujasite (FAD), type β (BEA), mordenite (MOR), ZSM-12 (MTW) and AlPO$_4$-5 (AFI). Examples of the zeolite having an ultra-large pore diameter (structure of oxygen 14-membered ring or more) may include UTD-1 (DON), CIT-5 (CFI) and VPI-5 (VFI). Of them, a zeolite having a medium pore diameter is preferable in order to improve the yield of propylene.

As the zeolite in the present embodiment, a metalloaluminosilicate obtained by replacing a part of aluminum atoms constituting a zeolite skeleton with an element(s) such as Ga, Fe, B, Cr and Ti, and a metallosilicate obtained by replacing the whole of aluminum atoms constituting a zeolite skeleton with the aforementioned elements, can be used. In such a case, $SiO_2/Al_2O_3$ (silica/alumina) molar ratio is calculated by converting the contents of the aforementioned elements in a metalloaluminosilicate or a metallosilicate to the molar numbers of alumina.

In the present embodiment, the non-conductive catalyst may contain a metal element. The non-conductive catalyst can contain at least one metal element selected from the group consisting of the metal elements belonging to the IB group of the periodic table. More specifically, a zeolite containing a metal corresponding to the IB-group metal in the state of ions in a catalyst or a zeolite containing the metal corresponding to the IB-group metal carried by the zeolite in a catalyst, can be used. A method for adding the IB-group metal element to a zeolite or a non-conductive catalyst is not particularly limited; a zeolite or a non-conductive catalyst containing no IB-group metal may be subjected to an ion exchange method known in the art. Examples of such method may include a liquid-phase ion exchange method and a solid-phase ion exchange method in which an impregnated supported catalyst is treated under a high temperature. In the case where the IB-group metal is added to a zeolite or a non-conductive catalyst by such an ion exchange method, a salt of the IB-group metal is preferably used. Examples of the salt of the IB-group metal may include silver nitrate, silver acetate, silver sulfate, copper chloride, copper sulfate, copper nitrate and gold chloride.

In the present embodiment, the non-conductive catalyst may contain a phosphorus element. The phosphorus element has an effect in suppressing dealumination of a zeolite. Particularly, dealumination tends to be accelerated if high temperature water vapor is used. Thus, a phosphorus element is preferably contained.

The content of a phosphorus element based on the total mass of the catalyst is preferably 0.01 mass % or more and 2.0 mass % or less and more preferably 0.01 mass % or more and 1.0 mass % or less. If the content of a phosphorus element is 0.01 mass % or more, the effect of suppressing dealumination under a high temperature water vapor atmosphere tends to be sufficiently ensured. In contrast, if the content is 2.0 mass % or less, corrosion of stainless steel under a high temperature water vapor atmosphere is rarely apparent. In the present embodiment, the content of a phosphorus element in a catalyst can be measured by an X-ray fluorescence spectrometer (RIX3000, manufactured by Rigaku) in accordance with a customary method. In the measurement, P-Kα beam can be used under the conditions: a bulb electric pressure of 50 kV and a bulb electric current of 50 mA.

[Silica]

In the present embodiment, the non-conductive catalyst and conductive catalyst preferably contain a silica carrier other than a zeolite in order to improve abrasion resistance thereof. As the silica carrier, a silica carrier classified in an inorganic porous carrier containing silica as a main component can be used. The "inorganic porous carrier containing silica as a main component" means that silica is contained in an amount of 60 mass % or more in an inorganic porous carrier. Note that the content refers to the value based on the whole mass of the carrier, in the condition that the component obtained by subtracting a zeolite from the non-conductive catalyst and conductive catalyst is regarded as the carrier. The content is preferably 80 mass % or more. The larger the amount of silica contained in the inorganic porous carrier, the more preferable since the abrasion resistance of the catalyst tends to be increased. The inorganic porous carrier may contain clay minerals such as kaolin, zirconia, titania and ceria, other than silica. The content of these elements based on the whole mass of the carrier is preferably 20 mass % or less, more preferably 10 mass % or less and further preferably 0 mass %. In short, the carrier containing only silica is particularly preferable.

In the present embodiment, the starting material for silica to be used as a carrier is not particularly limited and e.g., colloidal silica, water glass (sodium silicate) and fumed silica can be used. Since the amount of Na serving as a catalyst poison is low and handling is easy, colloidal silica is preferably used. Of them, a NH$_4$-stabilized colloidal silica is more preferably used from the same point of view.

[Shape of Catalyst]

In the present embodiment, the non-conductive catalyst and conductive catalyst preferably have a spherical shape in view of flowability and strength. The "spherical shape" does not necessarily refer to a "true sphere and close to a true sphere" but refers to "a shape having no outstanding projections and depressions and not a shape having a cavity (formed near the center) broken". However, it is preferable that as the shape of the catalyst, the closer to the true sphere by appearance, the more preferable. A spherical catalyst smoothly flows in a fluidized bed reactor. In addition, the spherical catalyst tends to be strong and also contributes to improvement of durability. Note that the spherical shape can be evaluated by observation of electron microscopic image of a catalyst and by measuring a repose angle of the catalyst (described later). The observation of electron microscopic image of a catalyst can be made by use of a scanning electron microscope (product name "S-800" manufactured by Hitachi, Ltd.) provided with an image processing system (high-definition image analysis filing system, product name, "IP-1000", manufactured by Asahi Kasei Corporation).

[Average Particle Size of Catalyst]

In the present embodiment, the non-conductive catalyst and the conductive catalyst preferably have an average particle size of 20 µm or more in order to obtain a small repose angle, which is an index of flowability of a catalyst, and satisfactory flowability in a fluidized bed reaction. In contrast, the non-conductive catalyst and the conductive catalyst have an average particle size of 300 µm or less, in order to obtain a sufficiently large mechanical strength and in order for the entire catalyst particles including the center portion to efficiently contribute to a fluidized bed reaction. Note that, if the average particle size of the catalyst is less than 20 µm, it is preferable that the catalyst particles have a particle size distribution where the particles having a particle size 2 times to 0.2 times as large as the average particle size occupy 80 mass % or more of the total particles, in order to improve flowability.

The "particle size" and "particle size distribution" herein are measured by a laser diffraction/scattering grading analyzer. The "average particle size" refers to a cumulative average diameter (median diameter), which is obtained by determining a particle size distribution (ratio of particles within a predetermined particle size zone) of a zeolite-containing catalyst powder by the aforementioned analyzer, obtaining a cumulative value of particle size distributions based on the total volume as 100%, and obtaining a particle size corresponding to 50% of the cumulative value.

[Electrostatic Deposition Rate of Catalyst]

A catalyst containing a zeolite and silica as main structural components has extremely low electric conductivity and easily charged. Particularly, the catalyst used in a fluidized bed is extremely easily charged since particles of the catalyst and a reactor repeatedly rubbed with each other. If the catalyst is charged, the catalyst deposits on a reactor wall surface and a stable height of the catalytic bed in the reactor does not obtained. The catalyst deposited on a reactor wall surface easily reaches a cyclone portion, which functions to separate a produced gas (from the reactor by a reaction) and the catalyst. As a result, the trapping efficiency of the cyclone reduces and the catalyst may possibly flow out from the reactor. In contrast, in the case of the catalyst containing a conductive substance according to the present embodiment, since the catalyst is conductive, electrostatic deposition of catalyst particles on the reactor is suppressed. The electrostatic deposition rate of the catalyst according to the present embodiment can be measured in the electrostatic deposition test described in Examples. If the electrostatic deposition rate of a catalyst is less than 15 mass %, catalyst deposition on a reactor, which produces a significant trouble in scale-up equipment, can be effectively suppressed. As a result, adjoint outflow toward an outlet pipe of the reactor can be effectively suppressed. Note that, in order to more effectively suppress the adjoint outflow of a catalyst, the electrostatic deposition rate is preferably 10 mass % or less.

Note that, in the present embodiment, if the electrostatic deposition rate obtained in an electrostatic deposition test is 15 mass % or more, the catalyst is defined as a "non-conductive catalyst", whereas, the electrostatic deposition rate is less than 15 mass %, the catalyst is defined as a "conductive catalyst".

In the present embodiment, the electrostatic deposition rate of a conductive catalyst can be controlled by the type or amount of conductive substance to be deposited. For example, a case where carbon coke is deposited on a non-conductive catalyst will be described. In order to obtain an electrostatic deposition rate of less than 15 mass %, it is preferable that about 4 mass % of carbon is deposited on a non-conductive catalyst. If the amount of carbon to be deposited is increased, the electrostatic deposition rate tends to decrease. Note that in order to sufficiently ensure a catalyst activity, the deposition amount of carbon is more preferably 4 mass % or more and 10 mass % or less. Note that the deposition amount of carbon can be evaluated by the method described in Examples (described later).

[Repose Angle of Catalyst]

In the present embodiment, the non-conductive catalyst and conductive catalyst preferably has a repose angle of 20° or more and 30° or less. If the repose angle falls within the range, satisfactory flowability is obtained, bridging between particles rarely occur and handling tends to be improved. In the present embodiment, the repose angle of a catalyst can be measured by the method described in Examples.

[Bulk Density of Catalyst]

In the present embodiment, as an index for a spherical degree of a spherical particle or a fluidization state thereof, the bulk density of a catalyst is preferably considered. In the present embodiment, the non-conductive catalyst and conductive catalyst have a bulk density of preferably 0.8 g/cm$^3$ or more and 1.3 g/cm$^3$ or less, more preferably 0.8 g/cm$^3$ or more and 1.2 g/cm$^3$ or less and further preferably 0.8 g/cm$^3$ or more and 0.95 g/cm$^3$ or less. If the catalyst having a bulk density within the above range is used in a fluidized bed reaction, reaction gas linear velocity is improved and the substance migration/heat transfer between a catalyst particle and a reaction gas tends to be more improved. Particularly, if the bulk density is 0.8 g/cm$^3$ or more, the ratio of particles of an awkward shape and broken, cracked and hollow particles tends to be reduced. In contrast, if the bulk density is 1.3 g/cm$^3$ or less, the reduction of chemical performance of a catalyst caused by reduction of a specific surface area tends to be successfully and effectively prevented. In the present embodiment, the bulk density of a catalyst is measured by the method described in Examples.

EXAMPLES

Now, the present invention will be more specifically described below by way of Examples and Comparative Examples; however, the present invention is not limited to these Examples.

The electrostatic deposition rate, repose angle and bulk density of catalysts of examples were measured as described below.

[Electrostatic Deposition Rate]

An electrostatic deposition test was performed as follows. As a test apparatus, a jet flow fluidization apparatus (manufactured by Gokou Seisaku-sho Kabushiki Kaisha) was used. This apparatus had a 10 µm Poremet filter at a gas inlet and had an inner diameter of 48.6 mm and a length of 450 mm. Note that the inner wall of the jet flow fluidization apparatus to face a measurement system was made of SUS316. The electrostatic deposition rate of a catalyst to the wall surface was obtained based on a change in differential pressure of powder flowage portion. With reference to a calibration curve prepared in advance by measuring the differential pressure values when a catalyst powder was introduced in a predetermined amount at regular intervals, an electrostatic deposition rate was calculated based on a decrease in differential pressure. More specifically, the differential pressure was measured by providing one of the differential pressure inlet pipes to the bottom portion of a catalyst powder flowage portion, and the other one was provided to the upper portion of a catalyst powder separation portion. As a differential pressure gage, a differential pressure transmitter, EJA110-DMS2A-20DC/K1 (manufactured by Yokokawa Electric Corporation) capable of measuring differential pressure up to 0 to 2 kPa was used. A catalyst powder (235 g) dried at 120° C. for 2 hours was loaded in the jet flow fluidization apparatus at room temperature and then nitrogen was introduced from a gas inlet at a rate of 15.3 NL/min. After the temperature of the powder flowage portion was set at 65° C., the differential pressure (differential pressure A) of the catalyst was measured. After nitrogen gas supply was continued at 65° C. for 24 hours, the differential pressure (differential pressure B) of the catalyst was measured. The electrostatic deposition rate was determined from the differential pressure A and B obtained as mentioned above, in accordance with the following formula.

Electrostatic deposition rate [mass %]=(1−$B$[kPa]/$A$ [kPa])×100

[Repose Angle]

A cylinder rotation system repose-angle measuring apparatus (manufactured by TSUTSUI SCIENTIFIC INSTRUMENTS CO., LTD.) was used for measurement. A 500 cc sample container (cylindrical measurement bottle) made of glass was charged with a catalyst (250 cc), and thereafter, the container was placed on a roller portion of the measuring apparatus such that the side surface of the cylindrical measurement bottle was in contact with the roller and the center axis of the cylindrical measurement bottle levelled off. Subsequently, while rotating the above roller portion around the center axis of the cylindrical measurement bottle at a rate of 2.4 rpm, the angle between the surface of the powder layer in the cylindrical measurement bottle and the horizontal surface was measured.

[Bulk Density]

A bulk specific gravity measuring apparatus (Z-2504-2000, manufactured by TSUTSUI SCIENTIFIC INSTRUMENTS CO., LTD.) was used for measurement. The bulk specific gravity measuring apparatus was placed in a horizontal site and a funnel (orifice 2.5 mmφ) was attached to a stand. Subsequently, tare mass (mass A) of a cylindrical cup (inner diameter: 30 mm, volume: 25 cm$^3$) was measured. On a receiver under the funnel, the cylindrical cup was placed. The funnel was gently charged with the catalyst (about 30 cc). The catalyst was allowed to pass the orifice of the funnel and drop in the cylindrical cup. When the catalyst overflew from the cylindrical cup, the operation of dropping the catalyst was stopped and excessive portion of the cylindrical cup was removed by e.g., a slide glass. The catalyst deposited on the outer surface of the cylindrical cup was brushed off and the mass (mass B) was accurately measured. The bulk density was obtained based on the obtained mass A and B in accordance with the following formula:

Bulk density [g/cm$^3$]=($B$[g]−$A$[g])/(cylindrical cup volume: 25 cm$^3$)

As the fluidized bed reactor used in Examples and Comparative Examples, a fluidized bed reactor of model number: 1R-15000, inner volume: 1.12 m$^3$, inner diameter: 400 mm, material: SUS304, manufactured by RYOKA WORKS was used. As the differential pressure gage provided to the fluidized bed reactor, a differential pressure transmitter, EJA110-DMS2B-30DD/JF3/G11/T12/Z (manufactured by Yokokawa Electric Corporation) capable of measuring differential pressure up to 0 to 20 kPa was used. As the thermolysis reactor in Examples and Comparative Examples, a thermolysis reactor of model code: U-shaped pipe electric furnace, inner diameter: 51.8 mm, total length: 16.9 m, material: KHR45A manufactured by SUKEGAWA ELECTRIC CO., LTD. was used.

A method for preparing a non-conductive catalyst containing a zeolite and silica used in Examples 1 to 3 and Comparative Examples 1 to 3 will be described below.

To 2000 g of colloidal silica (silica average particle size 5 nm, silica content: 15 mass %, Na content 185 ppm, manufactured by Nalco), 40 g of nitric acid (a reagent containing 60 mass % of nitric acid, manufactured by Wako Pure Chemical Industries Ltd.) was added and pH was controlled to 1.1. Thereafter, as a water soluble compound, 100 g of ammonium nitrate (special reagent, solubility to water (0° C.): 118 g/100 g water, manufactured by Wako Pure Chemical Industries Ltd.) was added. Subsequently, as a zeolite, 300 g of ZSM-5 containing SiO$_2$/Al$_2$O$_3$ in a molar ratio of 27 was added. In this manner, starting material slurry was prepared. The obtained starting material slurry was stirred at 25° C. for 3 hours. The state of the starting material slurry was sol. The starting material slurry was subjected to spray dry by a spray dryer to obtain a dry powder. The temperature of a fluid at the inlet of the spray dryer was set at 220° C. and the temperature of a fluid at the outlet of the spray dryer was set at 130° C. The starting material slurry was spray-dried in accordance to a rotary-disk system. The obtained dry powder was calcined by using an electric furnace at 700° C. for 5 hours under an air atmosphere. The resultant calcined powder was mixed with an aqueous nitric acid solution having a 0.1 mole concentration, controlled so as to obtain a 10 mass % solid substance concentration and subjected to ion exchange at 25° C. for one hour. After completion of the ion exchange, the resultant powder was sufficiently washed with water and dried at 120° C.

Non-conductive catalyst A1 thus obtained was subjected to measurement for an electrostatic deposition rate in accordance with the aforementioned method. As a result, the electrostatic deposition rate was 28.3 mass %. Furthermore, non-conductive catalyst A1 had a repose angle of 25° and a bulk density of 0.92 g/cm$^3$.

A method for preparing a non-conductive catalyst containing a zeolite and silica used in Example 4 and Comparative Example 4 will be described below.

To 16.08 kg of colloidal silica (silica average particle size 12 nm, silica content: 34 mass %, Na content 1 ppm, manufactured by Nalco), 0.32 kg of nitric acid (a reagent containing 60 mass % of nitric acid, manufactured by Wako Pure Chemical Industries Ltd.) was added and pH was controlled to 1.1. Thereafter, as a water soluble compound, 1.84 kg of ammonium nitrate (special reagent, solubility to water (0° C.): 118 g/100 g water, manufactured by Wako Pure Chemical Industries Ltd.) was added. Subsequently, as a zeolite, 19.86 kg of 27.7 mass % slurry of ZSM-5 containing SiO$_2$/Al$_2$O$_3$ in a molar ratio of 36, was added and further pure water (4.69 kg) was added to prepare starting material slurry. The obtained starting material slurry was stirred at 25° C. for 3 hours. The state of the starting material slurry was sol. The starting material slurry was subjected to spray dry by a spray dryer to obtain a dry powder. The temperature of a fluid at the inlet of the spray dryer was set at 220° C. and the temperature of a fluid at the outlet of the spray dryer was set at 130° C. The starting material slurry was spray-dried in accordance to a rotary-disk system. The obtained dry powder was calcined by using an electric furnace at 350° C. for one hour under an air atmosphere. A phosphate was attached to the obtained calcined powder as described below.

Diammonium hydrogen phosphate (3.95 g) (special reagent, solubility to 15° C. water: 131 g/100 g water, manufactured by Wako Pure Chemical Industries Ltd.) was dissolved in 150 g of pure water to prepare an aqueous phosphate solution (153.95 g). Subsequently, to the aqueous phosphate solution, the calcined powder (150 g) was added to prepare a solution mixture (303.95 g). Thereafter, vacuum dry was performed by a rotary evaporator at 80° C. and 250 Torr to 100 Torr. The obtained dry powder was calcined by using an electric furnace at 700° C. for one hour under an air atmosphere.

Non-conductive catalyst A2 thus obtained was subjected to measurement of an electrostatic deposition rate in accordance with the aforementioned method. As a result, the electrostatic deposition rate was 25 mass %. Furthermore, non-conductive catalyst A2 had a repose angle of 25° and a bulk density of 0.93 g/cm$^3$.

Example 1

A fluidized bed reactor was charged with the obtained non-conductive catalyst A1 (144 kg). To the fluidized bed reactor, a composition gas containing ethylene (30.5 mol %), steam (24.2 mol %) and nitrogen (45.3 mol %) was supplied in the conditions: a temperature of 500 to 530° C. and a pressure of 0.14 MPa·G, and at a gas flow rate of 0.34 m/sec to initiate a pretreatment step of non-conductive catalyst A1. Immediately after initiation of gas supply, a differential pressure gage indicated 11.2 kPa. (11.2 [kPa]×101.97 [(kg/m$^2$)/kPa]×reactor cross-sectional area 0.126 m$^2$=144 [kg] (initial charge amount)).

Forty eight hour later, the differential pressure gage indicated 11.9 kPa (11.9 [kPa]×101.97 [(kg/m$^2$)/kPa]×reactor cross-sectional area 0.126 m$^2$=153 [kg]). When the catalyst mass increased 1.06 times as large as that before the pretreatment, gas supply was stopped to terminate the pretreatment step. In this manner, a catalyst (153 kg), on which carbon coke (a ratio of about 5.9 mass %) was deposited, was obtained. Note that the deposition amount of carbon coke was obtained by using a thermogravimetry apparatus (thermal analysis apparatus main body: "MTC1000 type", manufactured by Mac Science; differential thermal balance: "TG-DTA2000 type" manufactured by Mac Science; thermal analysis system: "WS003", manufactured by Bruker AXS), based on a change in weight of a sufficiently dried catalyst attached with coke by calcination in air (the same shall apply in Examples and Comparative Examples below). After the above pretreatment step, the catalyst was collected and an electrostatic deposition rate was determined to be 6 mass %. It was confirmed that the catalyst was converted into a conductive catalyst.

Subsequently, the fluidized bed reactor was charged with the conductive catalyst (160 kg, differential pressure indication: 12.5 kPa) obtained in the above pretreatment step. To the fluidized bed reactor, a composition gas containing ethylene (30.0 mol %), steam (22.8 mol %) and nitrogen (47.2 mol %) was supplied in the conditions: a temperature of 550° C. and a pressure of 0.14 MPa·G, and at a gas flow rate of 0.70 m/sec to carry out a fluidized bed reaction.

Figure 2:
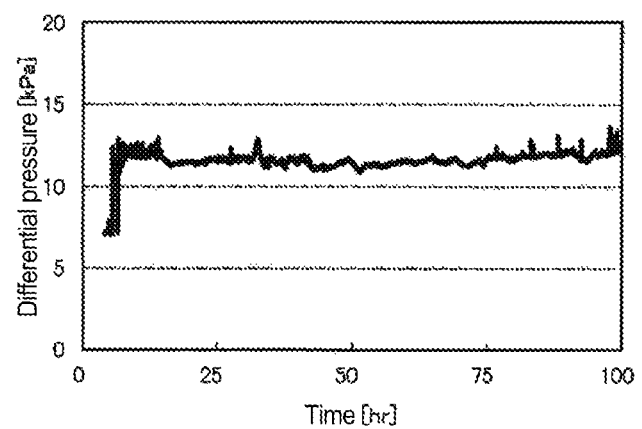
FIG. 2 shows a chart shown by a differential pressure gage provided in the fluidized bed reactor of Example 1.

FIG. 2 shows a chart indicated by the differential pressure gage during the above fluidized bed reaction. The differential pressure gage indicated stable values from the beginning to the end.

At the time point of 59.5 hr, and 72.7 hr after initiation of the reaction, the reaction product was introduced from the outlet of the reactor directly into a gas chromatograph (TCD, FID detector) to analyze the composition. The results were shown below. The aromatic hydrocarbon herein refers to an aromatic hydrocarbon (such as benzene, toluene, xylene) having 6 to 9 carbon atoms.

| Time (Hr) | 59.5 | 72.7 |
|---|---|---|
| Ethylene conversion rate (mass %) | 69.2 | 69.2 |
| Yield of propylene (mass %) | 22.0 | 22.6 |
| Yield of butene (mass %) | 13.3 | 13.6 |
| Yield of aromatic hydrocarbon (mass %) | 12.2 | 11.4 |

From the above results, it was found that triboelectric charging of the catalyst during a fluidized bed reaction can be suppressed by performing the pretreatment step for suppressing electrostatic charging of non-conductive catalyst A1, and that a fluidized bed reaction can be stably performed for a long time without problems such as flowability reduction and poor reaction results of the catalyst and adjoint outflow of the catalyst toward the outlet pipe of the reactor.

Example 2

A fluidized bed reactor was charged with the obtained non-conductive catalyst A1 (144 kg). To the fluidized bed reactor, a composition gas containing ethylene (30.5 mol %), steam (24.2 mol %) and nitrogen (45.3 mol %) was supplied in the conditions: a temperature of 500 to 530° C. and a pressure of 0.14 MPa·G, and at a gas flow rate of 0.34 m/sec to initiate a pretreatment step of non-conductive catalyst A1. Immediately after initiation of gas supply, a differential pressure gage indicated 11.2 kPa. (11.2 [kPa]×101.97 [(kg/m$^2$)/kPa]×reactor cross-sectional area 0.126 m$^2$=144 [kg] (initial charge amount)).

Forty one hour later, the differential pressure gage indicated 11.8 kPa (11.8 [kPa]×101.97 [(kg/m$^2$)/kPa]×reactor cross-sectional area 0.126 m$^2$=152 [kg]). When the catalyst mass increased 1.05 times as large as that before the pretreatment, gas supply was stopped to terminate the pretreatment step. In this manner, a catalyst (152 kg), on which carbon coke (a ratio of about 5.1 mass %) was deposited, was obtained. After the above pretreatment step, the catalyst was collected and an electrostatic deposition rate was determined to be 10 mass %. It was confirmed that the catalyst was converted into a conductive catalyst.

Subsequently, the fluidized bed reactor was charged with the conductive catalyst (160 kg, differential pressure indication: 12.5 kPa) obtained in the above pretreatment step. To the fluidized bed reactor, a composition gas containing ethylene (46 mol %), steam (23.9 mol %) and nitrogen (30.1 mol %) was supplied in the conditions: a temperature of 550° C. and a pressure of 0.14 MPa·G, and at a gas flow rate of 0.70 m/sec to carry out a fluidized bed reaction.

Figure 3:
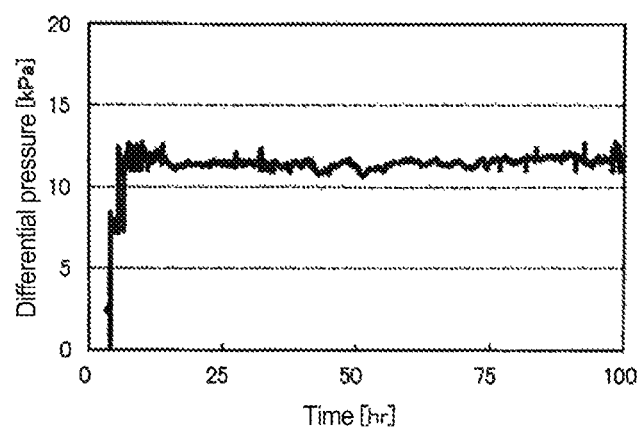
FIG. 3 shows a chart shown by a differential pressure gage provided in the fluidized bed reactor of Example 2.

FIG. 3 shows a chart indicated by the differential pressure gage during the above fluidized bed reaction. Like the Example 1, the differential pressure gage indicated stable values from the beginning to the end.

At the time point of 53.7 hr, and 89.0 hr after initiation of the reaction, the reaction product was introduced from the outlet of the reactor directly into a gas chromatograph (TCD, FID detector) to analyze the composition. The results were shown below. The aromatic hydrocarbon herein refers to an aromatic hydrocarbon (such as benzene, toluene, xylene) having 6 to 9 carbon atoms.

| Time (Hr) | 53.7 | 89.0 |
| --- | --- | --- |
| Ethylene conversion rate (mass %) | 70.9 | 68.9 |
| Yield of propylene (mass %) | 22.3 | 22.3 |
| Yield of butene (mass %) | 13.3 | 13.2 |
| Yield of aromatic hydrocarbon (mass %) | 13.3 | 12.9 |

Example 3

A fluidized bed reactor was charged with the obtained non-conductive catalyst A1 (144 kg). To the fluidized bed reactor, a composition gas containing ethylene (30.5 mol %), steam (24.2 mol %) and nitrogen (45.3 mol %) was supplied in the conditions: a temperature of 500 to 530° C. and a pressure of 0.14 MPa·G, and at a gas flow rate of 0.34 m/sec to initiate a pretreatment step of non-conductive catalyst A1. Immediately after initiation of gas supply, a differential pressure gage indicated 11.2 kPa. (11.2 [kPa]×101.97 [(kg/m$^2$)/kPa]×reactor cross-sectional area 0.126 m$^2$=144 [kg] (initial charge amount)).

Thirty five hour later, the differential pressure gage indicated 11.7 kPa (11.7 [kPa]×101.97 [(kg/m$^2$)/kPa]×reactor cross-sectional area 0.126 m$^2$=150 [kg]). When the catalyst mass increased 1.04 times as large as that before the pretreatment, gas supply was stopped to terminate the pretreatment step. In this manner, a catalyst (150 kg), on which carbon coke (a ratio of about 4.3 mass %) was deposited, was obtained. After the above pretreatment step, the catalyst was collected and an electrostatic deposition rate was determined to be 13.5 mass %. It was confirmed that the catalyst was converted into a conductive catalyst.

Subsequently, the fluidized bed reactor was charged with the conductive catalyst (160 kg, differential pressure indication: 12.5 kPa) obtained in the above pretreatment step. To the fluidized bed reactor, a composition gas containing ethylene (30.0 mol %), steam (22.8 mol %) and nitrogen (47.2 mol %) was supplied in the conditions: a temperature of 550° C. and a pressure of 0.14 MPa·G, and at a gas flow rate of 0.70 m/sec to carry out a fluidized bed reaction.

Figure 4:
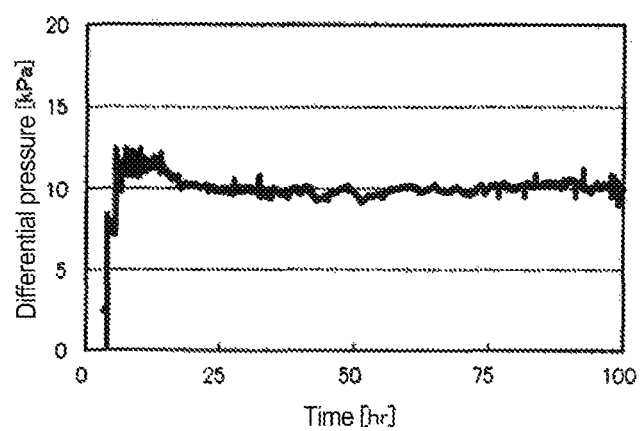
FIG. 4 shows a chart shown by a differential pressure gage provided in the fluidized bed reactor of Example 3.

FIG. 4 shows a chart indicated by the differential pressure gage during the above fluidized bed reaction. In a process where temperature was increased towards 550° C. (time after initiation of the reaction: 0 to 25 hr) after the fluidized bed reactor was charged with the catalyst, a phenomenon where the differential pressure of the catalytic bed decreases by 10 to 20% occurred and the tendency of the catalyst to be electrostatically charged was observed; however, in the following period (time after initiation of the reaction: 25 hr to 100 hr), the phenomenon of decreasing differential pressure of the catalytic bed no longer occurred, the fluidized bed reaction proceeded without problems.

At the time point of 47.5 hr, and 79.0 hr after initiation of the reaction, the reaction product was introduced from the outlet of the reactor directly into a gas chromatograph (TCD, FID detector) to analyze the composition. The results were shown below. The aromatic hydrocarbon herein refers to an aromatic hydrocarbon (such as benzene, toluene, xylene) having 6 to 9 carbon atoms.

| Time (Hr) | 47.5 | 79.0 |
| --- | --- | --- |
| Ethylene conversion rate (mass %) | 71.7 | 73.0 |
| Yield of propylene (mass %) | 22.5 | 22.6 |
| Yield of butene (mass %) | 13.4 | 13.4 |
| Yield of aromatic hydrocarbon (mass %) | 13.4 | 13.7 |

Comparative Example 1

A fluidized bed reactor was charged with the obtained non-conductive catalyst A1 (144 kg). To the fluidized bed reactor, a composition gas containing ethylene (30.5 mol %), steam (24.2 mol %) and nitrogen (45.3 mol %) was supplied in the conditions: a temperature of 500 to 530° C. and a pressure of 0.14 MPa·G, and at a gas flow rate of 0.34 m/sec to initiate a pretreatment step of non-conductive catalyst A1. Immediately after initiation of gas supply, a differential pressure gage indicated 11.2 kPa. (11.2 [kPa]×101.97 [(kg/m$^2$)/kPa]×reactor cross-sectional area 0.126 m$^2$=144 [kg] (initial charge amount)).

Twenty one hour later, the differential pressure gage indicated 11.5 kPa (11.5 [kPa]×101.97 [(kg/m$^2$)/kPa]×reactor cross-sectional area 0.126 m$^2$=148 [kg]). When the catalyst mass increased 1.03 times as large as that before the pretreatment, gas supply was stopped to terminate the pretreatment step. In this manner, a catalyst (148 kg), on which carbon coke (a ratio of about 2.6 mass %) was deposited, was obtained. After the above pretreatment step, the catalyst was collected and an electrostatic deposition rate was determined to be 17 mass %. The catalyst was not converted into a conductive catalyst (electrostatic deposition rate: less than 15 mass %).

Subsequently, the fluidized bed reactor was charged with the catalyst (160 kg, differential pressure indication: 12.5 kPa) obtained in the above pretreatment step. To the fluidized bed reactor, a composition gas containing ethylene (30.0 mol %), steam (22.8 mol %) and nitrogen (47.2 mol %) was supplied in the conditions: a temperature of 550° C. and a pressure of 0.14 MPa·G, and at a gas flow rate of 0.70 m/sec to carry out a fluidized bed reaction.

Figure 5:
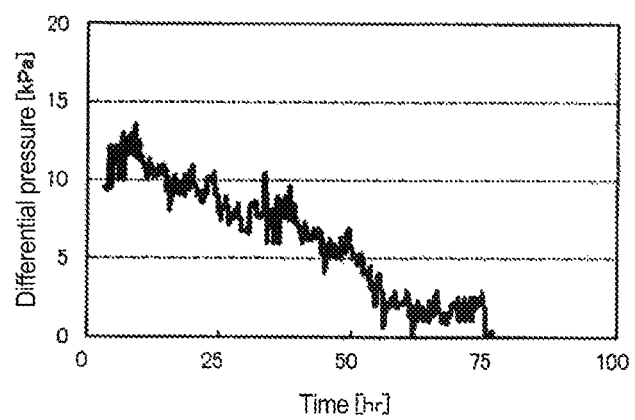
FIG. 5 shows a chart shown by a differential pressure gage provided in the fluidized bed reactor of Comparative Example 1.

FIG. 5 shows a chart indicated by the differential pressure gage during the above fluidized bed reaction. In a process where temperature was increased towards 550° C. (time after initiation of the reaction: 0 to 25 hr) after the fluidized bed reactor was charged with the catalyst, a phenomenon where the differential pressure of the catalytic bed decreases by 20 to 40% occurred and the tendency of the catalyst to be electrostatically charged was observed; in the following period, the phenomenon of decreasing differential pressure of the catalytic bed continued. At the time point of 75 hr after initiation of the reaction, the differential pressure decreased by 90% or more. As a result, the fluidized bed reaction was compulsively stopped. It was necessary to deal with collection of the catalyst that jointly flew out toward the outlet pipe of the reactor and cleaning of the outlet pipe of the reactor.

Comparative Example 2

A fluidized bed reactor was charged with the obtained non-conductive catalyst A1 (144 kg). To the fluidized bed reactor, a composition gas containing ethylene (30.5 mol %), steam (24.2 mol %) and nitrogen (45.3 mol %) was supplied in the conditions: a temperature of 500 to 530° C. and a pressure of 0.14 MPa·G, and at a gas flow rate of 0.34 m/sec to initiate a pretreatment step of non-conductive catalyst A1. Immediately after initiation of gas supply, a differential pressure gage indicated 11.2 kPa. (11.2 [kPa]×101.97 [(kg/m²)/kPa]×reactor cross-sectional area 0.126 m²=144 [kg] (initial charge amount)).

Fourteen hour later, the differential pressure gage indicated 11.4 kPa (11.4 [kPa]×101.97 [(kg/m²)/kPa]×reactor cross-sectional area 0.126 m²=147 [kg]). When the catalyst mass increased 1.02 times as large as that before the pretreatment, gas supply was stopped to terminate the pretreatment step. In this manner, a catalyst (147 kg), on which carbon coke (a ratio of about 1.8 mass %) was deposited, was obtained. After the above pretreatment step, the catalyst was collected and an electrostatic deposition rate was determined to be 20 mass %. The catalyst was not converted into a conductive catalyst (electrostatic deposition rate: less than 15 mass %).

Subsequently, the fluidized bed reactor was charged with the catalyst (160 kg, differential pressure indication: 12.5 kPa) obtained in the above pretreatment step. To the fluidized bed reactor, a composition gas containing ethylene (30.0 mol %), steam (22.8 mol %) and nitrogen (47.2 mol %) was supplied in the conditions: a temperature of 550° C. and a pressure of 0.14 MPa·G, and at a gas flow rate of 0.70 m/sec to carry out a fluidized bed reaction.

Figure 6:
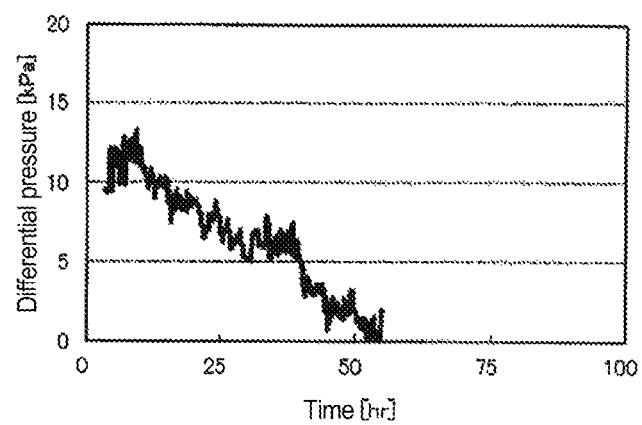
FIG. 6 shows a chart shown by a differential pressure gage provided in the fluidized bed reactor of Comparative Example 2.

FIG. 6 shows a chart indicated by the differential pressure gage during the above fluidized bed reaction. In a process where temperature was increased towards 550° C. (time after initiation of the reaction: 0 to 25 hr) after the fluidized bed reactor was charged with the catalyst, a phenomenon where the differential pressure of the catalytic bed decreases by 40 to 50% occurred and the tendency of the catalyst to be electrostatically charged was observed; in the following period, the phenomenon of decreasing differential pressure of the catalytic bed continued. At the time point of 50 hr after initiation of the reaction, the differential pressure decreased by 90% or more. As a result, the fluidized bed reaction was compulsively stopped. It was necessary to deal with collection of the catalyst that jointly flew out toward the outlet pipe of the reactor and cleaning of the outlet pipe of the reactor.

Comparative Example 3

A fluidized bed reactor was charged with the non-conductive catalyst A1 (160 kg, differential pressure indication: 12.5 kPa) obtained above. To the fluidized bed reactor, a composition gas containing ethylene (30.0 mol %), steam (22.8 mol %) and nitrogen (47.2 mol %) was supplied in the conditions: a temperature of 550° C. and a pressure of 0.14 MPa·G, and at a gas flow rate of 0.70 m/sec to perform a fluidized bed reaction.

Figure 7:
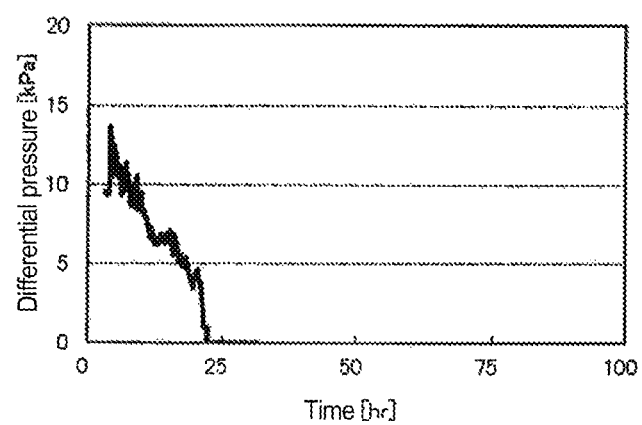
FIG. 7 shows a chart shown by a differential pressure gage provided in the fluidized bed reactor of Comparative Example 3.

FIG. 7 shows a chart indicated by the differential pressure gage during the above fluidized bed reaction. In a process where temperature was increased towards 550° C. (time after initiation of the reaction: 0 to 25 hr) after the fluidized bed reactor was charged with the catalyst, a phenomenon where the differential pressure of the catalytic bed decreases by 90% occurred and the tendency of the catalyst to be electrostatically charged was observed. As a result, the fluidized bed reaction was compulsively stopped. It was necessary to deal with collection of the catalyst that jointly flew out toward the outlet pipe of the reactor and cleaning of the outlet pipe of the reactor.

Example 4

The pretreatment step was performed in the same manner as in Example 1 except that the non-conductive catalyst was changed to A2, to obtain a catalyst (153 kg) to which carbon coke (at a ratio of about 5.9 mass %) was deposited. After the above pretreatment step, the catalyst was collected and an electrostatic deposition rate was determined to be 5 mass %. It was confirmed that the catalyst is converted into a conductive catalyst.

Subsequently, the fluidized bed reactor was charged with the catalyst (153 kg, differential pressure indication: 11.9 kPa) obtained in the above pretreatment step. To the fluidized bed reactor, an ethane decomposition gas (water content: 29 mass %) was supplied in the conditions: a temperature of 550° C. and a pressure of 0.14 MPa·G, and at a gas flow rate of 0.70 m/sec to carry out a fluidized bed reaction. As the ethane decomposition gas, an ethane decomposition gas, which was obtained by supplying ethane (130 kg/hr) heated to 600° C. and steam (52 kg/hr) to a thermolysis reactor as mentioned and performing a thermolysis reaction by controlling the outlet temperature of the thermolysis reactor at 825° C., and the outlet pressure at 0.20 MPa·G, was used by cooling it to 250° C.

Figure 8:
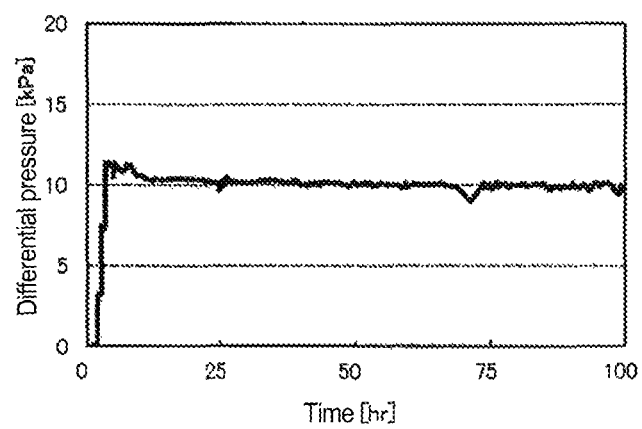
FIG. 8 shows a chart shown by a differential pressure gage provided in the fluidized bed reactor of Example 4.

FIG. 8 shows a chart indicated by the differential pressure gage during the fluidized bed reaction of Example 4. The differential pressure gage indicated stable values from the beginning to the end.

At the time point of 30 hr, and 60 hr after initiation of the reaction, the reaction product was introduced from the outlet of the reactor directly into a gas chromatograph (TCD, FID detector) to analyze the composition. The results were shown below. The aromatic hydrocarbon herein refers to an aromatic hydrocarbon (such as benzene, toluene, xylene) having 6 to 9 carbon atoms.

| Time (Hr) | 30.0 | 60.0 |
|---|---|---|
| Ethylene conversion rate (mass %) | 74.0 | 73.2 |
| Yield of propylene (mass %) | 24.0 | 24.8 |
| Yield of butene (mass %) | 11.8 | 12.4 |
| Yield of aromatic hydrocarbon (mass %) | 12.3 | 13.3 |

From the above results, it was found that triboelectric charging of the catalyst during a fluidized bed reaction can be suppressed by performing the pretreatment step for suppressing electrostatic charging of non-conductive catalyst A2, and that a fluidized bed reaction can be stably performed for a long time without problems such as flowability reduction and poor reaction results of the catalyst and adjoint outflow of the catalyst toward the outlet pipe of the reactor.

Comparative Example 4

A fluidized bed reaction was performed in the same manner as in Comparative Example 1 except that the non-conductive catalyst was changed to A2.

Figure 9:
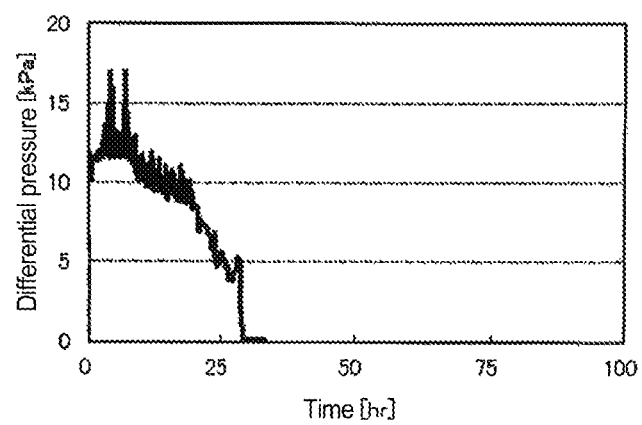
FIG. 9 shows a chart shown by a differential pressure gage provided in the fluidized bed reactor of Comparative Example 4.

FIG. 9 shows a chart indicated by the differential pressure gage during the fluidized bed reaction of Comparative Example 4. In a process where temperature was increased towards 550° C. (time after initiation of the reaction: 0 to 27 hr) after the fluidized bed reactor was charged with the catalyst, a phenomenon where the differential pressure of the catalytic bed decreases by 90% or more occurred and the tendency of the catalyst to be electrostatically charged was observed. As a result, the fluidized bed reaction was compulsively stopped. It was necessary to deal with collection of the catalyst that jointly flew out toward the outlet pipe of the reactor and cleaning of the outlet pipe of the reactor.

In Examples 1 to 4 and Comparative Examples 1 to 4, the results such as electrostatic deposition rates of the catalysts subjected to a fluidized bed reaction are shown in Table 1.

TABLE 1

|  |  | Differential pressure indication before the pretreatment [kPa] | Initial catalyst charge amount [kg] | Treatment time of pretreatment step [hr] | Differential pressure indication after the pretreatment [kPa] | Weight of catalyst after pretreatment [kg] | Weight increase ratio of catalyst [Times] | Carbon coke deposition rate [wt %] | Electrostatic deposition rate [wt %] |
|---|---|---|---|---|---|---|---|---|---|
| Example 1 | Catalyst A1 | 11.2 | 143.9 | 48 | 11.9 | 152.9 | 1.06 | 5.9 | 6 |
| Example 2 |  | 11.2 | 143.9 | 41 | 11.8 | 151.6 | 1.05 | 5.1 | 10 |
| Example 3 |  | 11.2 | 143.9 | 35 | 11.7 | 150.3 | 1.04 | 4.3 | 13.5 |
| Comparative Example 1 |  | 11.2 | 143.9 | 21 | 11.5 | 147.8 | 1.03 | 2.6 | 17 |
| Comparative Example 2 |  | 11.2 | 143.9 | 14 | 11.4 | 146.5 | 1.02 | 1.8 | 20 |
| Comparative Example 3 |  | 11.2 | 143.9 | 0 | 11.2 | 143.9 | 1.00 | 0.0 | 28 |
| Example 4 | Catalyst A2 | 11.2 | 143.9 | 48 | 11.9 | 152.9 | 1.06 | 5.9 | 5 |
| Comparative Example 4 |  | 11.2 | 143.9 | 0 | 11.2 | 143.9 | 1.00 | 0.0 | 25 |

The present application is based on Japanese Patent Application No. 2012-178398 filed on Aug. 10, 2012, the content of which is incorporated herein by reference.

INDUSTRIAL APPLICABILITY

According to the present invention, in a fluidized bed reaction using a non-conductive catalyst, electrostatic charging of a catalyst in a reactor is suppressed and catalyst deposition to the reactor can be reduced.

REFERENCE SIGNS LIST 1 fluidized bed reactor
2 gas supply pipe
3 pipe provided downstream of a reactor
4 #1 cyclone
5 #2 cyclone
6 differential pressure gage
7 feed gas
8 product gas
9 catalytic bed

The invention claimed is:

1. A method for converting an olefin or an alcohol, comprising:
   a pretreatment step of obtaining a conductive catalyst, which has an electrostatic deposition rate of less than 15 mass %, by
      charging a fluidized bed reactor with a non-conductive catalyst having an electrostatic deposition rate of 15 mass % or more,
      supplying a heated hydrocarbon gas to the fluidized bed reactor, and
      depositing a conductive substance comprising carbon on the non-conductive catalyst; and
   a step of converting the olefin or the alcohol by a fluidized bed reaction using the conductive catalyst,
   wherein, in the pretreatment step, a gas supply rate is 0.40 m/sec or less in terms of gas flow rate in the fluidized bed reactor, and
   in the step of converting the olefin or the alcohol, a gas supply rate is 0.5 m/sec or more in terms of gas flow rate during the fluidized bed reaction.

2. The method for converting the olefin or the alcohol according to claim 1, wherein the non-conductive catalyst comprises a zeolite and/or silica.

3. The method for converting the olefin or the alcohol according to claim 1, wherein the olefin comprises ethylene.

4. A method for producing propylene or an aromatic compound, comprising a step of obtaining propylene or the aromatic compound by the method according to claim 1.

5. The method for converting the olefin or the alcohol according to claim 1, wherein the non-conductive catalyst has a repose angle of 20° or more and 30° or less.

6. The method for converting the olefin or the alcohol according to claim 1, wherein the non-conductive catalyst has a bulk density of 0.8 g/cm$^3$ or more and 1.3 g/cm$^3$ or less.

7. The method for converting the olefin or the alcohol according to claim 1, wherein the deposition amount of carbon on the conductive catalyst is 4 mass % or more and 10 mass % or less.

* * * * *